United States Patent [19]

Hui et al.

[11] Patent Number: 5,330,718
[45] Date of Patent: Jul. 19, 1994

[54] SENSOR ELEMENT AND METHOD FOR MAKING THE SAME

[75] Inventors: Henry K. Hui, Laguna Niguel; Charles S. Bankert, Oceanside, both of Calif.

[73] Assignee: Puritan-Bennett Corporation, Carlsbad, Calif.

[21] Appl. No.: 960,903

[22] Filed: Oct. 14, 1992

Related U.S. Application Data

[63] Continuation-in-part of Ser. No. 758,291, Aug. 28, 1991, Pat. No. 5,219,527, which is a continuation of Ser. No. 394,638, Aug. 16, 1989, abandoned.

[51] Int. Cl.$^5$ .................................................. G01N 21/64
[52] U.S. Cl. .................................. 422/82.07; 128/634; 385/13; 427/2.12; 427/2.13; 422/82.06; 422/82.08; 436/68; 436/166
[58] Field of Search ............... 422/58, 57, 82.06–82.08; 385/13; 427/2; 436/68, 166; 128/634

[56] References Cited

U.S. PATENT DOCUMENTS

| | | |
|---|---|---|
| Re. 31,879 | 5/1985 | Lubbers et al. ........... 436/133 |
| 3,904,373 | 9/1975 | Harper . |
| 4,003,707 | 1/1977 | Lubbers et al. . |
| 4,194,877 | 3/1980 | Peterson ..................... 8/4 |
| 4,200,110 | 4/1980 | Peterson et al. ........... 128/634 |
| 4,344,438 | 8/1982 | Schultz ..................... 128/634 |
| 4,468,229 | 8/1984 | Su ............................ 8/507 |
| 4,557,900 | 12/1985 | Heitzmann .................. 422/55 |
| 4,568,518 | 2/1986 | Wolfbeis et al. ........... 422/56 |
| 4,657,736 | 4/1987 | Marsoner et al. .......... 422/56 |
| 4,712,865 | 12/1987 | Hsu et al. . |
| 4,849,172 | 7/1989 | Yafuso et al. .............. 422/55 |
| 4,867,919 | 8/1989 | Yafuso et al. .............. 264/1.5 |
| 4,906,249 | 3/1990 | Fogt et al. .................. 8/647 |
| 4,921,589 | 5/1990 | Yates et al. ................. 204/157 |
| 4,925,268 | 5/1990 | Iyer et al. . |
| 5,219,527 | 6/1993 | Hui et al. .................... 422/82.06 |
| 5,252,494 | 10/1993 | Walt ........................... 422/82.06 |

FOREIGN PATENT DOCUMENTS

| | | |
|---|---|---|
| 0105870A2 | 4/1984 | European Pat. Off. . |
| 0283206A2 | 9/1988 | European Pat. Off. . |
| 0336986A1 | 10/1989 | European Pat. Off. . |
| WO 88/05533 | 7/1988 | PCT Int'l Appl. . |
| 2132348A | 7/1984 | United Kingdom . |

OTHER PUBLICATIONS

G. G. Vurek; Fiber–Optic Carbon Dioxide Partial Pressure Sensor; Mar. 1983; PB83-189738.

*Primary Examiner*—Jill A. Johnston
*Attorney, Agent, or Firm*—Fulwider Patton Lee & Utecht

[57] ABSTRACT

A sensor element includes an analyte-permeable matrix which supports and maintains an emulsion of a sensing solution containing an analyte-sensitive indicator substance in a plurality of tiny vesicles. The sensing solution is immiscible with the matrix material, and contains a dye indicator which dissociates into two different species. The sensing solution is initially mixed with an agent which modifies the equilibrium of dissociation of the dye indicator for optimal sensitivity. The liquid matrix preferably includes a curing inhibitor to allow the matrix to remain liquid until applied to a sensing surface, such as the tip of an optical fiber. The sensing solution remains suspended in these homogeneously dispersed vesicles after the matrix solidifies.

25 Claims, 1 Drawing Sheet

SENSOR ELEMENT AND METHOD FOR MAKING THE SAME

RELATED APPLICATIONS

This is a continuation in part of Ser. No. 07/758,291, filed Aug. 28, 1991, which issued as U.S. Pat. No. 5,219,527 on Jun. 15, 1993, and which was a continuation of Ser. No. 07/394,638, filed Aug. 16, 1989, now abandoned.

FIELD OF THE INVENTION

The present invention relates generally to instruments for measuring the concentration of elements, compounds and gases in a fluid or gaseous mixture, and more particularly relates to a method for homogeneously dispersing an analyte-sensitive indicator substance throughout an analyte-permeable matrix using emulsion-related techniques. The method produces an improved sensor element that is particularly suitable for use with a number of methods and instruments for measuring the content of an analyte in a sample.

DESCRIPTION OF RELATED ART

The development of instruments and methods for measuring the concentration of elements and compounds in liquids and gaseous mixtures has been a tremendous breakthrough in many science-related fields, particularly the medical arts. Medical instruments are available for performing in vivo measurements of blood chemistry to determine, for example, pH and the partial pressures of gases, such as carbon dioxide and oxygen, in a patient's blood stream. These instruments use specially adapted catheters, optical fibers and sensor elements that can be placed directly in a blood vessel, muscle, or other body tissue of a patient. These implanted devices are generally safe, economical, and can be manufactured from material that permits long term implantation in the body. As a result, physicians can continually monitor the blood chemistry of a patient, eliminating the need to constantly draw blood for laboratory analysis.

Many different forms of analyte-measuring instruments have been designed and developed throughout the years for use in numerous medical and industrial applications. Among the many methods and instruments used are those that rely on optical properties of the sensing element which contains a dye that is sensitive to a particular analyte. When the dye interacts with the analyte in a liquid or gaseous sample, the dye undergoes a physical change that is directly measurable. This change is usually a physical property of the dye, such as its luminescence intensity, fluorescence intensity, or decay time. The change of this physical property is directly related to the concentration of the analyte in the sample.

The analyte-sensitive substance, also called an indicator, is arranged in a sensor element having a covering formed by permeable membrane which allows the analyte to permeate and interact with the indicator while preventing other analytes and fluids from reaching the indicator. The sensor element is usually first placed in the test sample to allow the analyte to interact with the indicator and then is then subjected to an external source of excitation, usually a beam of light. The change in the intensity of response of the indicator dye is directly related to the change in the physical characteristic of the indicator due to interaction with the analyte. Since a change in the concentration of the analyte is directly related to the change in intensity of response of the indicator dye, the intensity of the dye indicator response can be used to calculate the proportion of the analyte present in the sample.

Early devices utilized a monochromatic light beam to determine the intensity of fluorescence of the indicator. These devices used optical lenses and prisms for focusing the monochromatic light onto an external sensing element, which included a permeable membrane, much like an envelope or bladder, which contained the indicator substance. This membrane acted as a barrier which separated the indicator substance from the fluid being analyzed. While somewhat successful, these early instruments presented a number of problems which hindered performance. For example, these membranes were particularly vulnerable to development of slight cracks either during storage or use, causing the indicator to leak out. Also, the indicator had a tendency to leach out of the membrane, especially if the membrane came in contact with a substance having similar properties. As a result of this leakage, the response of the indicator would change and affect the accuracy of any measurement.

The development of glass or optical fibers provided a new source for directing the light source to the sensor element. Optical fiber sensing instruments utilize a similar principle for determining the content of an analyte in a sample. Light generated from an external instrument travels along the optical fiber to the sensor element incorporating the indicator substance which is placed at the distal end of the fiber. The fluorescence emission is then transmitted back from the sensing element to an external detection instrument that measures the change of fluorescence intensity of the indicator.

Other optical systems utilize multiple optical fibers and a sensor element that is remotely located on a catheter or similar device. These systems include at least one light transmitting optical fiber which is placed in close alignment with the remote sensor element and a second output fiber that carries the light from the sensor to the external detection instrument.

The use of optical fibers required the development of new sensor elements that could be contained in a compact geometry. These elements had to be, of course, much smaller than the conventional bladder-type sensor. Also, due to the thin diameter of the fiber, the use of bladders or envelops were generally not feasible due to their relatively large size. Some bladder retaining sensors were developed, but suffered from the same leaking and leaching problems that confronted the earlier sensors.

Alternative solutions for creating a usable sensor included dispersing particles containing an indicator in an analyte-permeable matrix. These sensors proved to be much smaller than conventional sensors, but they too had similar problems of leaching and were vulnerability to cracks that allow the indicator to leak from the matrix. Other disadvantages included uneven distribution of the indicator throughout the matrix which caused variations between sensors made from similar materials.

Accordingly, those concerned with the development and use of optical fiber sensing devices have recognized the need for improving the sensor element which contains the indicator substance. The sensor element should have an even dispersion of the indicator throughout the permeable membrane and should not be vulnerable to small cracks that could render the sensor useless. Preferably, an improved sensor element should be capable of easy application to an optical fiber and should be capable of being mass produced in a thin profile. It would therefore be desirable for the analyte permeable matrix to have an extended working pot life as a liquid, which can be applied and cured quickly to a solidified form.

Optical fiber sensors for measuring pH and the partial pressure of carbon dioxide may utilize a single fluorescent or absorbance indicator dye that dissociates into a protonated or acid, form and an unprotonated or base form, each having a different physical response characteristic. For such a fluorescent dye indicator sensitive to acidity, changes in the pH or partial pressure of carbon dioxide causes the pKa of the dye indicator to change, representing a change in the equilibrium between the different forms of the dye indicator, thereby changing the intensity of the light emission or absorbance response by at least one of the acid-base forms at characteristic wavelengths.

The carbon dioxide content of a solution may, for example, be measured with an optical fiber sensor utilizing a dye indicator which dissociates into such acid and base forms, such as fluorescein as a fluorescence indicator, or phenol red as an optical absorbance indicator, enclosed in a semipermeable silicone matrix at the end of an optical fiber. Carbon dioxide will permeate through this silicone matrix to the indicator substance. Another type of fluorescence indicator which has been used for measuring pH and carbon dioxide content of a sample is hydroxypyrenetrisulfonic acid (HPTS).

The concentration of carbon dioxide in a solution can generally be determined by such an optical sensor by measuring the pH of a solution of bicarbonate in equilibrium with the carbon dioxide in the solution. The bicarbonate and carbon dioxide form a pH buffer system in which the hydrogen ion concentration generally varies with the carbon dioxide concentration. Although various buffer systems have been used in such sensors for maintaining a buffer range of from about 7.0 to about 8.0, compatible with the response range of the dye being used, exposure of such systems to carbon dioxide changes the equilibrium of the two species of the dye indicator, changing the effective pH buffer range. Thus, for purposes of monitoring blood analytes in physiological ranges with optimal sensitivity with dissociative dye indicators having different species with at least one of those species having a measurable physical characteristic sensitive to the concentration of the analyte of interest, it would be desirable to include a dye indicator dissociation modifier in the analyte sensing solution to provide optimal sensitivity of the dye indicator to physiological levels of the analyte in the blood. It would also be desirable to further alter the equilibrium to change the extent of dissociation of the dye indicator to be slightly outside the range desired for measuring physiological blood analyte levels before exposure of the sensing solution to the analyte, such that exposure of the dye indicator to the analyte of interest will bring the equilibrium of dissociation of the indicator into an optimal range of sensitivity to physiological levels of the analyte.

SUMMARY OF THE INVENTION

Briefly, and in general terms, the present invention provides for a sensor element formed with a dye indicator matrix having tiny vesicles of an analyte sensing solution dispersed within an analyte permeable matrix. The method of making the sensor utilizes techniques in emulsion technology to form the vesicles within the permeable matrix. The sensing solution is formed from a solvent which is immiscible with the matrix material, and contains a dye indicator which dissociates into two different species. The sensing solution is initially mixed with an agent which modifies the equilibrium of dissociation of the dye indicator for optimal sensitivity. The sensing solution may also contain an emulsive substance that enhances the emulsification of the dye indicator in the sensing solution and thereby substantially reduces the miscibility of the dye indicator in the material that makes up the matrix. Both the sensing solution and the matrix material are vigorously mixed together in liquid form, so that the sensing solution will be homogeneously dispersed in tiny vesicles throughout the matrix material. The matrix material also preferably includes a curing inhibitor to allow the matrix to remain liquid for application to a surface, such as the tip of an optical fiber. The matrix material containing the vesicles of sensing solution is then preferably heat cured to solidify the matrix material in place on the sensing surface, while the sensing solution in the vesicles remains suspended in liquid form within the matrix.

The resulting structure provides a sensor element that should remain substantially unimpaired should a slight crack develop in the matrix during use or in storage. In the event that a slight crack does develop, the matrix will expose the sensing solution in only a small number of vesicles, leaving the majority of vesicles unimpaired and ready for use. The result is a superior sensor element with optimal sensitivity that can be used over and over again even if one or more cracks develops in its structure. Similar cracks would render most prior art sensors unusable.

The size of each vesicle can also be quite small to allow the sensor element to be manufactured in an extremely thin profile. The size of the vesicle will depend on how well the sensing solution is dispersed in the liquid matrix material. The sensing solution can, for example, be mixed with high shear into the matrix to increase the number of vesicles while reducing their size. Alternatively, if larger vesicles are desired, the matrix need not be mixed as rapidly with the sensing solution to reduce the number of vesicles, thereby increasing their size. In this fashion, the mixture of the sensor solution with the matrix can be directly varied to increase or decrease the size of the vesicles.

In one form of the present invention, the vesicles preferably have a diameter in the range of from about 0.5 microns to about 10 microns, and the sensor element is made with a matrix that has a thickness that is only slightly larger then the size of the smallest vesicle, typically with a thickness of from about 5 microns to about 50 microns. Such a sensor will provide sufficient exposure of the indicator within the matrix and will result in a sensor with an ultra thin profile.

The matrix material containing the vesicles of sensing solution can be directly applied onto the end of an optical fiber, or it can be manufactured as a separate element that can be used with existing or larger size measuring instruments that utilize large external sensors. Variation between various kinds of different sensors can thus be decreased due to the homogeneous dispersion of the sensing solution within the matrix material.

The matrix can be made from a hydrophobic material which is essentially impervious to ions but which will transmit sufficient water vapor over time to permit rehydration of the sensing solution in the vesicles of the sensor. Sensors manufactured in accordance with the present invention may be stored dry and then rehydrated over a period of several hours. Such a sensor has clear advantages over those prior art sensors which must be kept hydrated throughout the manufacturing and storage periods.

In one preferred aspect of the invention, the aqueous sensing solution includes a dye indicator which undergoes a dissociation into two different species in equilibrium in the sensing solution which is sensitive to the presence of the analyte, and an agent for modifying the equilibrium of dissociation of the dye indicator to an optimal range of sensitivity to the analyte is preferably added to the sensing solution. At least one species of the dye indicator will react to produce an emission of light in response to exposure to an external excitation through the matrix, with the intensity of emission of light being related to the content of the analyte in the sample. The extent of dissociation of the dye indicator is also preferably adjusted to a level outside the optimal range of sensitivity, before exposure to the analyte, such that when the dye indicator is exposed to the analyte of interest the equilibrium of dissociation of the indicator will be within the optimal range of sensitivity of the dye indicator to the analyte.

In another form of the invention, the sensor element can contain vesicles of two distinct sensing solutions with different dye indicators for sensing two different analytes, such as carbon dioxide and oxygen blood gases. Typical indicators which can be used for sensing blood oxygen include coronene and decacyclene, and the mutually immiscible solvents of the two sensing solutions may be water and silicone, for example. The two sensing solutions are also immiscible with the matrix material, so that they can be evenly dispersed throughout the matrix. This allows a single sensor matrix to be used to detect two analytes. Of course, the matrix must be selected from materials that will be permeable to the additional analyte as well.

From the above, it may be seen that the present invention provides a new and useful sensor element and method for preparing the same for detecting the concentration of one or more analytes in a fluid or gaseous mixture by the use of indicators that are physically responsive to an analyte and can be exposed to an external excitation, such as light to measure the physical response. Other features and advantages of the present invention will become apparent from the following detailed description, taken in conjunction with the accompanying drawings, which illustrate, by way of example, the principles of the invention.

DETAILED DESCRIPTION OF THE PREFERRED EMBODIMENTS

The sensor element of the present invention utilizes an analyte permeable matrix which supports a sensing solution including an analyte sensitive dye indicator in a plurality of vesicles that are homogeneously dispersed throughout the matrix. The structure is an advance over prior art sensors since the sensor is less susceptible to slight cracks that may develop in the matrix. A slight crack only has a minimal effect on the sensor element since only sensing solution from a small number of vesicles will be released, while the majority of vesicles will remain intact and capable of functioning normally.

The sensing solution preferably contains a dye indicator which undergoes a dissociation into two species which is sensitive to the analyte of interest. The dye indicator is also preferably mixed with an agent for modifying the equilibrium between the two species of the dye indicator for optimal sensitivity to the analyte. The sensing solution is immiscible with the matrix material, and may include an emulsifier that enhances the solution of the dye indicator in the sensing solution, to substantially prevent the dye indicator in the solution from leaching through the liquified matrix material when the sensing solution and matrix material are mixed. The dye indicator in the sensing solution is provided with optimal sensitivity to the analyte, and is thus "suspended" in vesicles in the liquid matrix material. The sensor solution and matrix material can be vigorously stirred to reduce the size of the vesicles, and for a more even dispersion of the sensing solution in the matrix. The emulsion is preferably heat cured after being placed on a sensing surface, to solidify the matrix with the sensing solution still suspended in liquid form within its structure. The resulting structure creates a sensing element which provides ample exposure of the two species of the analyte sensitive indicator to an external source excitation, such as a beam of light.

Figure 1:
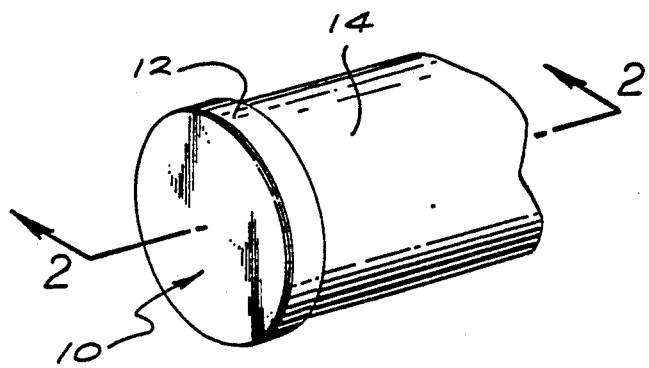
FIG. 1 is a perspective view of a sensor element made in accordance with present invention as it is affixed to the end of an optical fiber.

FIG. 1 illustrates a general arrangement of a sensor element 10 made in accordance with the present invention as it is affixed to a free end 12 of an optical fiber 14. This sensor element 10 and a fiber 14 are specifically designed for use with measuring instruments that utilize a light source for measuring the change of intensity of the fluorescence of at least one of the two species of the analyte-sensitive dye. Generally, the sensor and the fiber are placed in a sample of fluid or gaseous mixture which contains a certain concentration or content of the analyte that is desired to be measured. Alternatively, due to their small size, the sensor and optical fiber can be easily placed within a blood vessel, tissue or muscle of a patient for in vivo measurement of the analyte.

Figure 2:
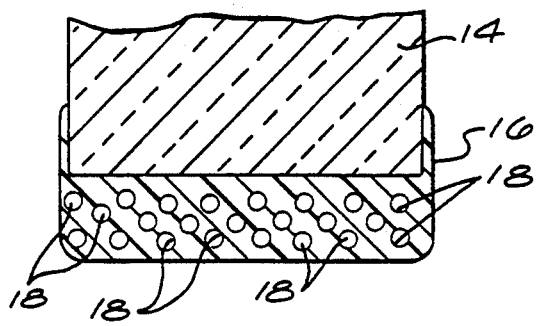
FIG. 2 is an enlarged cross-sectional view of the sensor element shown in FIG. 1 and taken along line 2—2.

Referring to FIG. 2, the sensor element 10 includes a matrix 16 through which a plurality of vesicles 18 are homogeneously dispersed. Each of these vesicles contains a minute amount of sensing solution including an indicator substance that is sensitive to the analyte being measured. In a preferred embodiment, the analyte of interest is carbon dioxide, and the sensing solution comprises an aqueous solution of 14 mmolar hydroxypyrenetrisulfonic acid (HPTS) which dissociates into acid and base forms responsive to the pH of the sensing solution. As will be explained further below, the sensing solution preferably also includes an agent for modifying the pKa of HPTS, where pKa represents the extent of dissociation of the dye indicator. The term pKa is defined as the negative logarithm of the equilibrium constant, K, for the dissociation reaction of the dye indicator, for purposes of this application. The agent for modifying the pKa of the indicator dye to have optimal sensitivity is preferably 10% polyvinylpyrrolidone (PVP), which also functions to enhance the emulsification of the dye indicator in the aqueous sensing solution. Other agents for modifying the pKa of the indicator dye may also be used. For the purpose of sensing carbon dioxide content of a blood sample, the sensing solution is preferably aqueous, and also preferably includes a 35 mmolar bicarbonate buffer. The sensing solution is further preferably titrated with a base to have a pH of about 9.0 before exposure to carbon dioxide. The aqueous phase contained in the vesicles preferably comprises from about 10% to about 20% of the total dye indicator—matrix emulsion. These vesicles 18 are thoroughly dispersed within the matrix 16 to insure that a sufficient amount of indicator substance is exposed within the matrix to the irradiating light that will be transmitted through the optical fiber.

The matrix 16 is preferably formed from a material that is selectively permeable to the particular analyte that is being measured. The matrix acts much like a protective barrier which separates the sensing solution from the fluid or gas mixture that is being analyzed, allowing only the desired analyte to permeate to the sensing solution while preventing other fluids and gases from reaching the solution. The matrix is preferably formed from a material that is hydrophobic, to protect the integrity of the sensing solution from ionic species in the sample being tested. A typical hydrophobic material that is suitable for use is silicone, such as polydiphenyldimethylsioloxane, or polysiloxane, for example. Other types of silicones may also be suitable, although silicone is just one example of a suitable material that can be used for the matrix. Silicone is permeable to a number of gases and is available in a liquid form that is preferably cross-linked to form a semi-soft solid matrix. Silicone is ideal for use as a matrix since the aqueous sensing solution can be easily dispersed in the silicone in its liquid form, and the emulsion can then be directly applied to an optical fiber where the matrix can be heat cured to its solid form.

In use, light of a certain wavelength is transmitted to the optical fiber 14 from an external instrument (not shown). The excitation light irradiates the encapsulated indicator substance, and a fluorescence emission from the indicator is transmitted back to an external instrument (not shown) that measures the intensity of the fluorescence of the indicator. In this manner, the measure of the intensity can be used to calculate the concentration of the analyte in the sample. Since the indicator is well dispersed throughout the sensor element, the difference in the intensity of the light attributable to the presence of the analyte will be an accurate measure of the concentration in the sample.

The benefits of utilizing numerous vesicles in the matrix becomes apparent if a slight crack should develop in the sensor element during use or while the element is in storage. A slight crack in the matrix will only expose the sensing solution in a small number of vesicles, leaving the majority of vesicles essentially unimpaired and capable of performing its designed function. As a result, the present invention can still be used over and over again if cracks develop within the matrix.

The size of the vesicles also determines the minimum thickness in which the sensor element can be manufactured. During the stirring of the sensing solution with the liquid matrix material, the size of the vesicles of the sensing solution can be varied depending upon the rate at which the solution is stirred with the matrix material. For instance, if smaller vesicles are desired, then the sensing solution must be vigorously stirred with the matrix to decrease the size of the vesicles. This increases the number of vesicles as well. If larger vesicles are required, then the intensity of the stirring of the sensing solution and matrix material would have to be reduced. Correspondingly, when the size of the vesicles is increased, the number of them decreases. The vesicles preferably have a diameter in the range of from about 0.5 microns to about 10 microns.

In one embodiment of the present invention, the sensor element can be manufactured having a thickness that is only slightly larger than the size of the smallest vesicle that can be formed within the matrix. In this embodiment, the sensor element is thus preferably made with a matrix having a thickness of from about 5 microns to about 50 microns. This can be a desirable structure in those applications which require certain size limitations for the sensor.

It should be appreciated that the indicator substance is not necessarily limited to fluorescent compounds. The sensor may also use an indicator that experiences a change in its absorption, luminescence, or phosphorescence, for example. The choice of the indicator substance will depend on the analyte that is being measured and the particular application contemplated for the sensor element.

Figure 3:
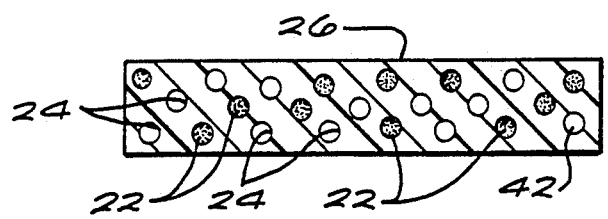
FIG. 3 is a cross-sectional view of another embodiment of a sensor element made in accordance with the present invention which utilizes two distinct sensing solutions with different dye indicators for detecting two different analytes.

FIG. 3 shows an alternative embodiment of a sensor element in which two distinct sensing solutions 22 and 24 containing different dye indicator substances are disposed in a plurality of vesicles dispersed throughout the matrix 26. In this form of the invention, the matrix 26 is made from a material that is permeable to the two analytes that are to be tested, such as carbon dioxide and oxygen blood gases. Typical dye indicators which can be used for sensing oxygen in such a second sensing solution include coronene and decacyclene, for example. Each sensing solution is immiscible with the matrix material, and the sensing solutions are also mutually immiscible, to prevent the two solutions from blending together.

Figure 4:
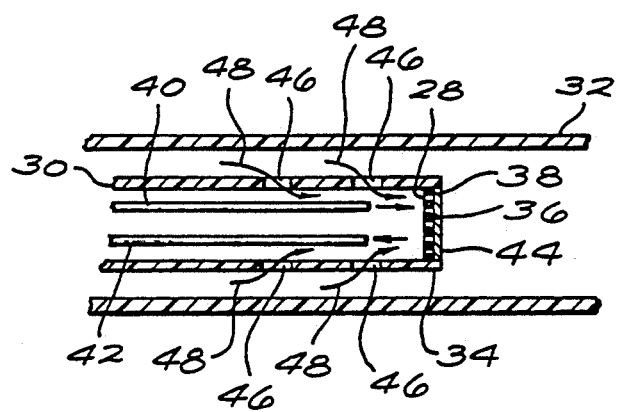
FIG. 4 is a partial cross-sectional side view of a sensor element made in accordance with the present invention that can be used with multiple optical fiber systems that can be placed in a blood vessel of a patient.

FIG. 4 shows an alternative embodiment of the present invention in which a sensor element 28 is contained within a catheter 30 that is placed in a blood vessel 32 of a patient. This sensing element 28 is located near the distal end 34 of the catheter 30 and is structured as a thin membrane which supports the sensing solution within vesicles 36 formed in a permeable matrix 38. In this particular embodiment, the sensor element is just slightly larger than the size of a vesicle. This enables the analyte to penetrate through the matrix much easier and interact with the analyte-sensitive indicator substance contained within the vesicles.

This particular sensor element is made accessible to an optical fiber 40 which transmits the irradiating light to the sensor 28. A separate optical fiber 42 for carrying the light back to a detection instrument located outside the patient is also utilized. In this particular arrangement, an additional reflector 44 may be placed behind the sensor element 28 to help reflect the irradiating light back to the optical fiber 42. In practice, a single fiber which transmits and returns the irradiating light may be used.

The catheter shown in FIG. 4 includes a number of openings 46 which allows blood to travel and permeate through the permeable matrix. All in all, the embodiment shows the adaptability and versatility of a sensor element built in accordance with the present invention and how it can be modified for used with different measuring systems.

In a preferred method of making the sensor element of the invention, an aqueous solution which is immiscible with the matrix material is mixed with a dye indicator, such as HPTS, and an agent for modifying the pKa of the dye indicator, such as polyvinylpyrrolidone, as will be further explained below. The aqueous solution containing the dye indicator is immiscible with the particular material used to form the matrix. Emulsifiers which may be added to the sensing solution in accordance with the present invention to enhance emulsification of the dye indicator in the sensing solution may be a water soluble or water swellable polymer, such as polyethylene glycol, and polyethylene oxide. The resultant sensing solution can be vigorously stirred into the liquid matrix material to cause the formation of the numerous vesicles of sensing solution in the matrix material. The number of vesicles and their size can be directly varied by changing the intensity with which the solution and matrix materials are stirred. For example, if many vesicles of a small size are desired, then the two compounds must be vigorously stirred together. Conversely, the number of vesicles can be easily decreased by simply decreasing the intensity in which the solution is stirred with the matrix. In this manner, tiny vesicles containing the sensing solution are dispersed within the matrix material where they will remain in liquid form after the matrix material cures.

The matrix material also preferably comprises a liquid silicone containing a curing inhibitor to prevent the matrix material from prematurely solidifying, so that the dye indicator matrix emulsion can be easily applied to a surface, such as an optical fiber. The dye indicator— matrix emulsion is preferably heat cured for rapid setting of the matrix. The matrix material is also preferably cross-linked to form a solid material. In such a case, an appropriate amount of cross linker should be added to the emulsion prior to curing.

Before the matrix material solidifies, a specially prepared optical fiber is preferably dipped into the emulsion to form the sensor element at the end of the fiber. Once the fiber is dipped into the emulsion, it can be removed and heat cured to solidify the matrix.

The following examples are included for further understanding of the invention. It should be understood that these examples are by no way intended to limit the scope of the present invention.

EXAMPLE 1

The following example illustrates the preparation of a sensor element which can be used to detect an analyte such as carbon dioxide. Initially, five grams of polyvinylpyrrolidone (40000 mw) were dissolved in an aqueous solution of 0.01M hydroxypyrenetrisulfonic acid (HPTS) in 0.1M sodium bicarbonate. A sample of 1.5 grams of the resulting compound was added to 10 grams of Petrarch PS783 liquid silicone. These two components were stirred, utilizing a high speed homogenizer, for one minute at the highest setting. A small aliquot of platinum catalyst (0.005 g) was also added to the homogenized mixture. The mixture was again homogenized for an additional minute at the highest shear rate. A 0.5 gram portion of the resulting emulsion was hand mixed with 0.05 g of Petrarch PS123 cross-linker.

The cured compound was placed in a saline solution and 2.64% carbon dioxide bubbled through the solution. When a sample was irradiated with 460 nm light, the fluorescence emission at 515 nm yielded a normalized voltage of 4.481 V on a detector. When the concentration of carbon dioxide was increased to 8.2% carbon dioxide, the resulting normalized voltage was 3.316 V. This indicates a functioning carbon dioxide sensor.

EXAMPLE 2

An aqueous solution was formulated by preparing a 10% solution of PVP in deionized water. The PVP solution was then titrated to pH 7. HPTS and $NaHCO_3$ were added to the PVP solution to give the aqueous solution concentrations of 14 mmolar HPTS and 35 mmolar $NaHCO_3$. By mixing the HPTS dye indicator with the 10% PVP solution, the pKa of the dye was shifted from pH 7.4 to 8.0. The buffer system of PVP and 35 mmolar $NaHCO_3$ help to provide optimal sensitivity to the physiological range of carbon dioxide levels.

The aqueous solution was then titrated until a pH of 9 was reached. The aqueous solution was then passed through a 0.2 micron filter and stored in a dark and cool environment. By titrating the PVP solution to pH 7 and the buffered HPTS mixture to pH 9, the pH of the carbon dioxide sensing solution is preset to 9 prior to exposure to any carbon dioxide gas. When the sensor is eventually exposed to carbon dioxide gas, the pH of the buffered sensing solution falls within the pH range from 7 to 8, which provides for an optimal dye sensitivity range to physiological carbon dioxide levels.

The silicone portion of the formulation was prepared by adding 0.24% curing inhibitor (D6210, Huls America catalog number) and 0.015% catalyst as in Example 1, to polydiphenyldimethylsiloxane (PS782, Huls America). The inhibitor provides the silicone with an extended liquid pot life, for application to an optical fiber or other sensing surface.

The aqueous sensing solution was then vigorously stirred with the liquid silicone mixture by homogenizing the two components at a high shear speed. The resulting emulsion was then mixed with 10% crosslinker (PS123, Huls America) by weight. The resulting dye indicator matrix emulsion has a useful liquid pot life of over 24 hours due to the action of the inhibitor.

A decladded, prepared optical fiber was then dipped in the dye indicator matrix emulsion and heat cured in an oven at a temperature of from 180 to 220 degrees Centigrade for from 5 to 20 seconds.

From the above, it is evident that the present invention provides a means for preparing a sensor element that evenly distributes an indicator substance throughout an analyte permeable matrix. The resulting sensor is superior over prior art devices due to the even distribution of indicator. While particular form of the invention has been described and illustrated, it will also be apparent to those skilled in the art that various modifications may be made without departing from the spirit and scope of the invention. Accordingly, it is not intended that the invention be limited, except as by the appended claims.

We claim:

1. A sensor element for sensing carbon dioxide in a sample comprising:

an optical fiber having a surface portion covered with a matrix made from a hydrophobic material that is permeable to carbon dioxide; and a plurality of vesicles dispersed throughout said matrix, each of said vesicles containing an aqueous sensing solution including a dye indicator which dissociates into two different species in response to the presence of carbon dioxide, an agent for modifying the equilibrium of dissociation of said dye indicator to be within a range for optimal sensitivity to said carbon dioxide, and an aqueous base for raising the pH of said aqueous sensing solution to be outside a physiological range of carbon dioxide concentration when said dye indicator is not exposed to carbon dioxide, and to be within said physiological range of carbon dioxide concentration when said dye indicator is exposed to carbon dioxide, said dye indicator being exposable to an external excitation through said matrix, and at least one species of said dye indicator producing an emission of light in response to said excitation, with said emission of light being related to the content of carbon dioxide in said sample, whereby exposure of the dye indicator to carbon dioxide will cause the equilibrium of dissociation of the indicator to be within said range for optimal sensitivity.

2. The sensor element as defined in claim 1, wherein said agent for modifying the equilibrium of dissociation of said dye indicator is polyvinylpyrrolidone.

3. The sensor element as defined in claim 1, wherein said matrix is only sightly thicker than the size of one of said vesicles in said matrix.

4. The sensor element as defined in claim 1 wherein said sensing solution and said matrix material are mutually immiscible.

5. The sensor element as defined in claim 1 wherein said vesicle are homogenous dispersed throughout said matrix.

6. The sensor element as defined in claim 1 wherein said matrix material is silicone.

7. The sensor element as defined in claim 1, wherein said dye indicator is a fluorescent dye indicator.

8. The sensor element as defined in claim 1, further comprising a plurality of vesicles containing a second sensing solution containing a second dye indicator responsive to said excitation to produce a second emission of light related to the content of a second analyte in said sample, with said emissions of light from said indicator dyes being of different wavelength ranges, and said first aqueous sensing solution and said second sensing solution being mutually immiscible.

9. A sensor element for sensing carbon dioxide content of a sample comprising:

an optical fiber having a surface portion covered with a matrix made from a hydrophobic material that is permeable to carbon dioxide; and a plurality of vesicles dispersed throughout said matrix, each of said vesicles containing an aqueous sensing solution including polyvinylpyrrolidone, an aqueous base, and a dye indicator which undergoes dissociation into two different species, said dissociation being sensitive to carbon dioxide, said aqueous sensing solution having a pH set to approximately 9 before exposure to carbon dioxide gas, said dye indicator being exposable to an external excitation through said matrix, and said dye indicator producing an emission of light in response to said excitation, with said emission of light being related to the content of carbon dioxide in said sample.

10. The sensor element as defined in claim 9, wherein said matrix is only sightly thicker than the size of one of said vesicles in said matrix.

11. The sensor element as defined in claim 9, wherein said sensing solution and said matrix material are mutually immiscible.

12. The sensor element as defined in claim 9, wherein said vesicle are homogenous dispersed throughout said matrix.

13. The sensor element as defined in claim 9, wherein said matrix material comprises diphenyldimethylpolysiloxane.

14. The sensor element as defined in claim 9, wherein said dye indicator is a fluorescent dye indicator.

15. The sensor element as defined in claim 9, wherein said dye indicator is hydroxypyrenetrisulfonic acid.

16. The sensor element as defined in claim 9, further comprising a plurality of vesicles containing a second sensing solution containing a second dye indicator responsive to said excitation to produce a second emission of light related to the content of a second analyte in said sample, with said emissions of light from said indicator dyes being of different wavelength ranges, and said first aqueous sensing solution and said second sensing solution being mutually immiscible.

17. A method for making a sensor element for sensing an analyte in a sample, said sensor including an optical fiber having a surface portion covered with a matrix made from a material that is permeable to the analyte, and a plurality of vesicles dispersed throughout said matrix, each of said vesicles containing an aqueous sensing solution including a fluorescent dye indicator which has an equilibrium of dissociation into two different species which is sensitive to said analyte, comprising the steps of:

adding said fluorescent dye indicator substance that is sensitive to said analyte to an aqueous solution and an agent for modifying the equilibrium of dissociation of said dye indicator substance to be within an optimal range of sensitivity to said analyte;

adding an aqueous base to said aqueous solution to change the pH of said aqueous solution to be outside an optimal range of sensitivity of said dye indicator substance in said aqueous solution to form said aqueous sensing solution;

adding said aqueous sensing solution to a liquid silicone matrix containing a curing inhibitor for prolonging the liquid state of said matrix;

homogeneously dispersing the aqueous solution throughout said liquid matrix solution to form an emulsion of said sensing solution in a plurality of vesicles in said liquid matrix;

coating said surface of said optical fiber with said emulsion; and heating said emulsion to cure said matrix of said emulsion into a solid semi-permeable membrane that is permeable to said analyte.

18. The method of claim 17, wherein said surface of said optical fiber is coated with a thickness of said dye indicator matrix only slightly more than the size of one of said vesicles.

19. The method of claim 17, further comprising the step of adding a curing catalyst to said liquid matrix.

20. The method of claim 17, further comprising the steps of adding a second sensing solution containing a second dye indicator responsive to a second analyte to said liquid matrix and said first aqueous sensing solution, said first sensing solution and said second sensing solution being mutually immiscible, and homogeneously dispersing said first and second sensing solutions in said liquid matrix to form a plurality of vesicles in said liquid matrix containing said first sensing solution and a plurality of vesicles containing said second sensing solution.

21. A method for making a sensor element for sensing the carbon dioxide content of a sample, said sensor including an optical fiber having a surface portion covered with a matrix made from a material that is permeable to carbon dioxide, and a plurality of vesicles dispersed throughout said matrix, each of said vesicles containing an aqueous sensing solution including polyvinylpyrrolidone and a fluorescent dye indicator responsive to carbon dioxide, comprising the steps of:

adding polyvinylpyrrolidone and said fluorescent dye indicator substance that is sensitive to carbon dioxide to an aqueous solution;

titrating said aqueous solution containing polyvinylpyrrolidone and said dye indicator with an aqueous base to a pH of 9 to form said aqueous sensing solution;

adding said aqueous sensing solution to a liquid silicone matrix containing a curing inhibitor for prolonging the liquid state of said matrix;

homogeneously dispersing the aqueous solution throughout said liquid matrix to form an emulsion of said sensing solution in a plurality of vesicles in said liquid matrix;

coating said surface of said optical fiber with said emulsion in a thickness slightly more than the size of one of said vesicles; and heating said emulsion to a temperature between about 180 and 220 degrees Centigrade to cure said matrix into a solid semi-permeable membrane that is permeable to carbon dioxide.

22. The method of claim 21 further comprising the step of adding a curing catalyst to said liquid matrix.

23. The method of claim 21 further comprising the steps of adding a second sensing solution containing a second dye indicator sensitive to a second analyte to said liquid matrix and said first aqueous sensing solution, said first sensing solution and said second sensing solution being mutually immiscible, and homogeneously dispersing said first and second sensing solutions in said liquid matrix to form a plurality of vesicles containing said first sensing solution and a plurality of vesicles in said liquid matrix containing said second sensing solution.

24. A sensor element for sensing an analyte in a sample comprising:

an optical fiber having a surface portion covered with a matrix made from a material that is permeable to the analyte;

a first plurality of vesicles dispersed throughout said matrix, each of said vesicles containing an aqueous sensing solution including a first dye indicator which dissociates into two different species in response to the presence of said analyte, and an agent for modifying the equilibrium of dissociation of said first dye indicator to be within a range for optimal sensitivity to said analyte, said first dye indicator being exposable to an external excitation through said matrix, and at least one species of said first dye indicator producing an emission of light in response to said excitation, with said emission of light being related to the content of said analyte in said sample; and a second plurality of vesicles containing a second sensing solution including a second dye indicator responsive to said excitation to produce a second emission of light related to the content of a second analyte in said sample, with said emissions of light from said indicator dyes being of different wavelength ranges, said first aqueous sensing solution and said second sensing solution being mutually immiscible.

25. A sensor element for sensing carbon dioxide content of a sample comprising:

an optical fiber having a surface portion covered with a matrix made from a material that is permeable to carbon dioxide;

a first plurality of vesicles dispersed throughout said matrix, each of said vesicles containing an aqueous sensing solution including polyvinylpyrrolidone and a first dye indicator which undergoes dissociation into two different species, said dissociation being sensitive to carbon dioxide, said aqueous sensing solution having a pH set to approximately 9 before exposure to carbon dioxide gas, said dye indicator being exposable to an external excitation through said matrix, and said dye indicator producing an emission of light in response to said excitation, with said emission of light being related to the content of carbon dioxide in said sample, and a second plurality of vesicles containing a second sensing solution including a second dye indicator responsive to said excitation to produce a second emission of light related to the content of a second analyte in said sample, with said emissions of light from said indicator dyes being of different wavelength ranges, said first aqueous sensing solution and said second sensing solution being mutually immiscible.

* * * * *

UNITED STATES PATENT AND TRADEMARK OFFICE
CERTIFICATE OF CORRECTION

PATENT NO. : 5,330,718
DATED : July 19, 1994
INVENTOR(S) : Henry K. Hui, Charles S. Bankert It is certified that error appears in the above-indentified patent and that said Letters Patent is hereby corrected as shown below:

Column 1, line 64, delete "and then", insert --and--;

Column 2, line 58, delete "vulnerability", insert --vulnerable--;

Column 9, line 8, delete "used", insert --use--;

Column 11, line 35, insert --,-- before "wherein";

Column 11, line 38, insert --,-- before "wherein";

Column 11, line 39, delete "homogenous", insert --homogenously--;

Column 11, line 41, insert --,-- before "wherein";

Column 12, line 12, delete "homogenous", insert --homogenously--.

Signed and Sealed this

Tenth Day of January, 1995

*Attest:*

BRUCE LEHMAN

*Attesting Officer*  *Commissioner of Patents and Trademarks*